United States Patent [19]

Kline

[11] 4,341,211
[45] Jul. 27, 1982

[54] LUBRICATING OBJECT APPLICATOR

[76] Inventor: Larry H. Kline, 18 Broad St., Suite 805, Charleston, S.C. 29401

[21] Appl. No.: 300,028

[22] Filed: Sep. 8, 1981

[51] Int. Cl.³ .................... A61M 35/00; A61M 5/00
[52] U.S. Cl. ................................ 128/261; 128/220; 128/237; 128/264; 128/271
[58] Field of Search ............. 128/260, 271, 220, 224, 128/234, 237, 238

[56] References Cited

U.S. PATENT DOCUMENTS 2,017,334 10/1935 Ackerman .
2,747,574 5/1956 DeLorenzo .
3,139,886 7/1964 Tallman et al. ..................... 128/263
3,335,725 8/1967 Gordon .
3,378,008 4/1968 Ogle ..................................... 128/220
3,537,451 11/1970 Gordon .
3,840,010 10/1974 Giglio .
3,882,866 5/1975 Zackheim .......................... 128/261

*Primary Examiner*—C. Fred Rosenbaum
*Attorney, Agent, or Firm*—Larry Harold Kline

[57] ABSTRACT

A device and method are disclosed for placing an object into a body cavity comprising an applicator body, a lubricating plunger securable within the applicator body, and an object plunger, which is operative to move the object through the applicator body into the body cavity.

60 Claims, 17 Drawing Figures

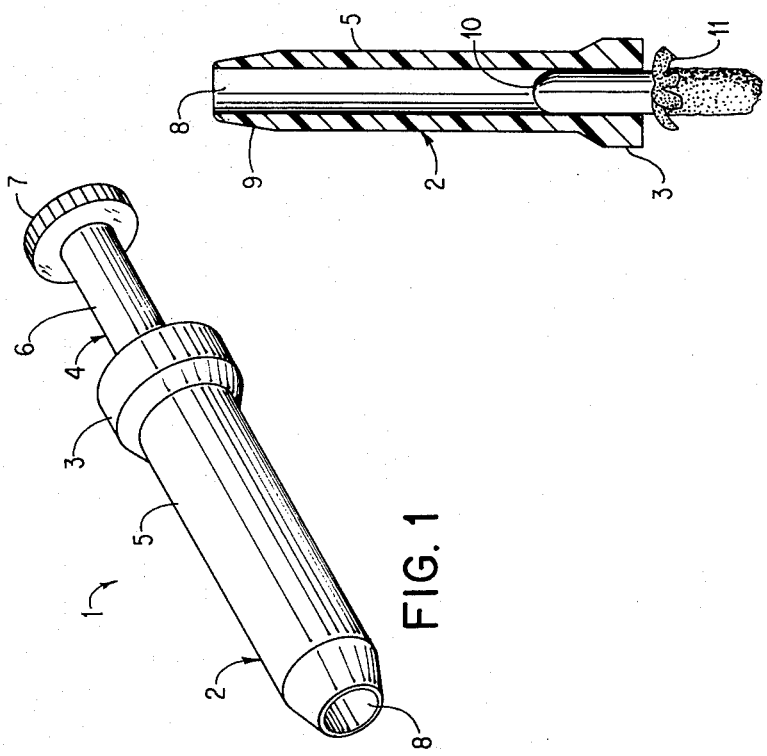

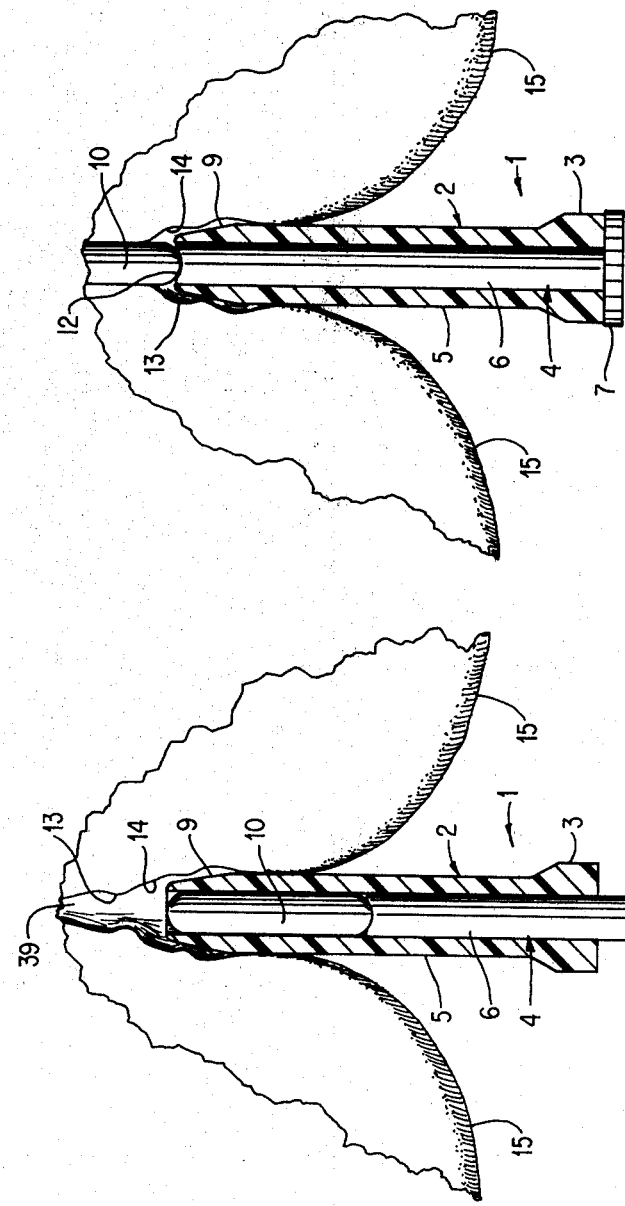

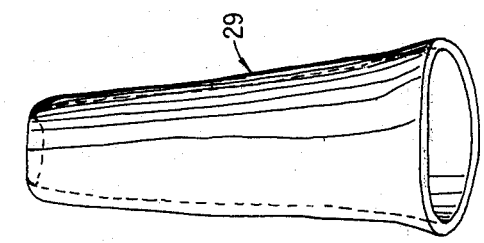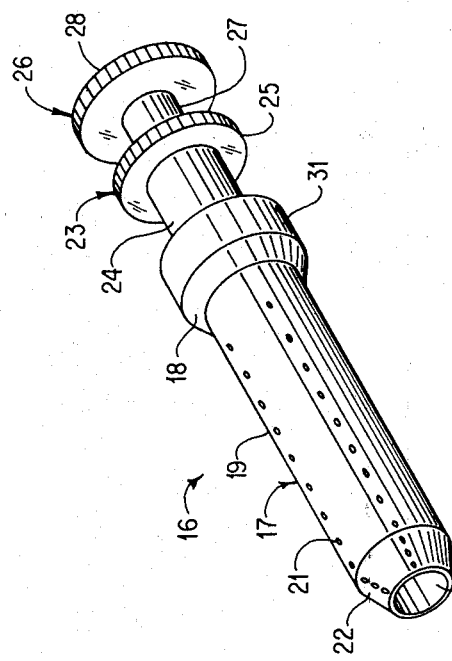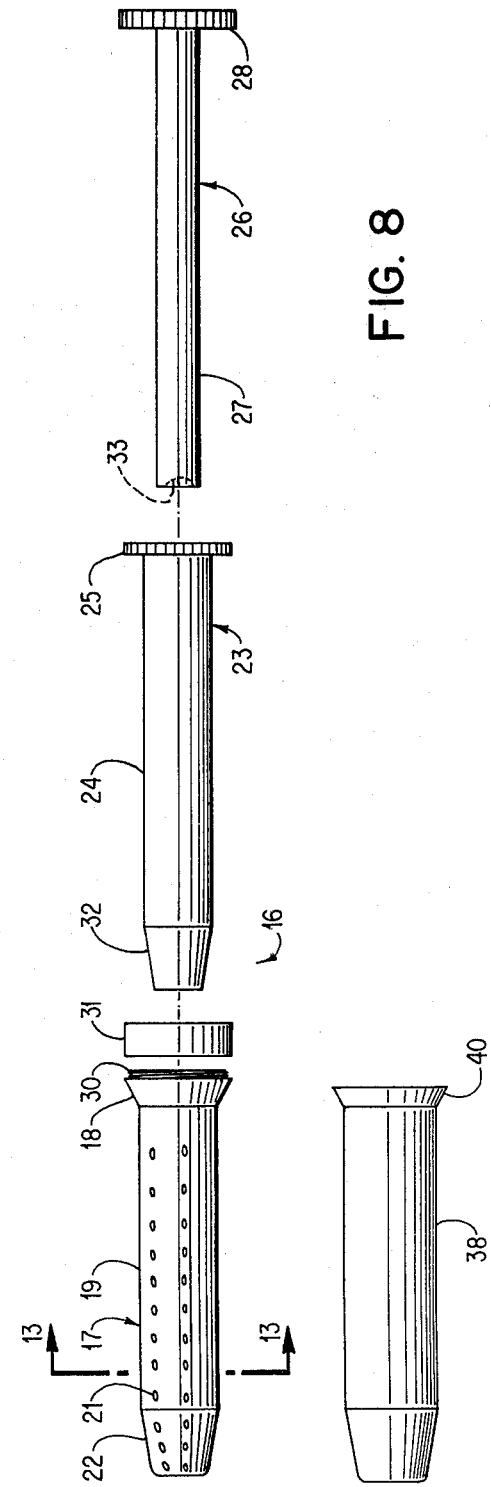

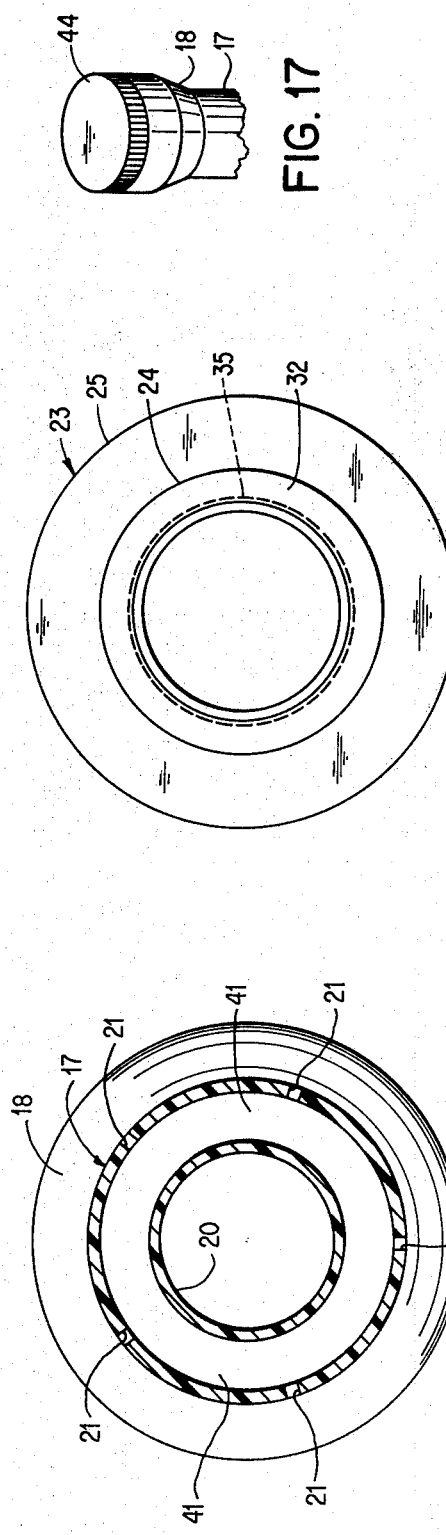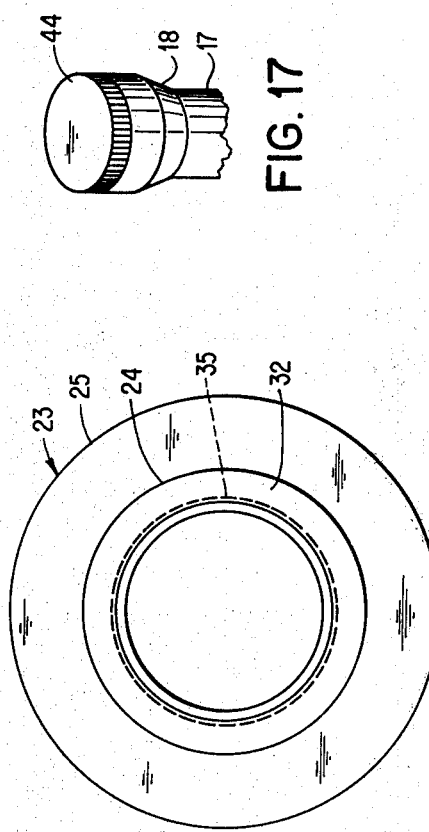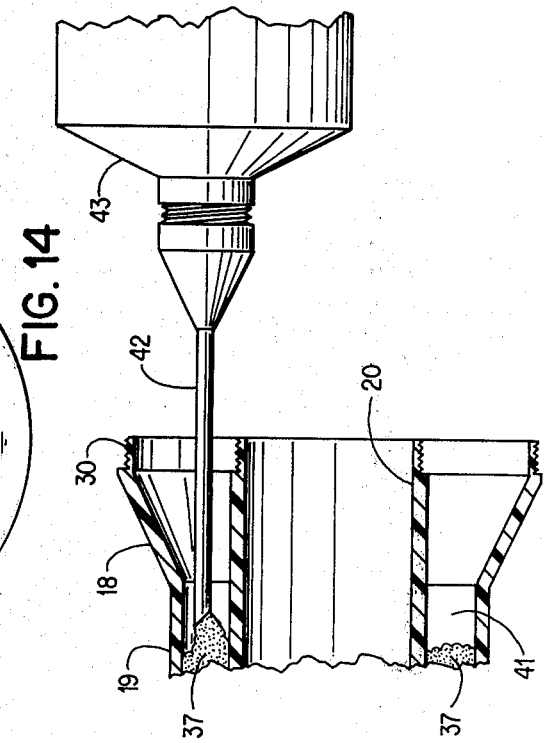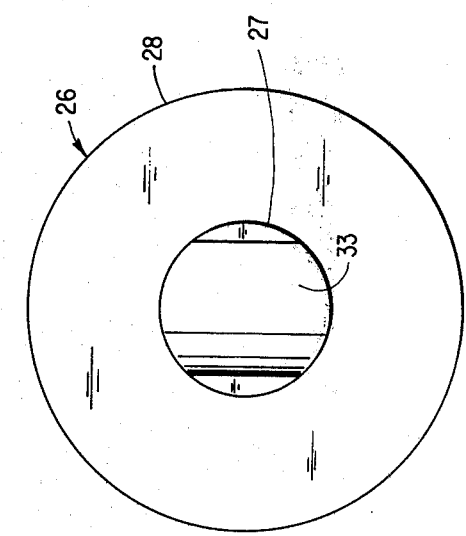

LUBRICATING OBJECT APPLICATOR

This invention relates to a suppository applicator and more particularly to a suppository applicator which can be self-lubricating.

Constipation, diarrhea, pregnancy and over-exertion are common physical causes of hemorrhoids. Certain occupations that require continued standing or sitting also contribute to that condition. Most hemorrhoidal flare-ups are minor and may last for several days and can be self-treated. Presently, hemorrhoidal conditions are treated by the use of cream or suppositories. The cream or suppository may be placed or injected into the anus. Hemorrhoids are internal or external varicose veins in the anal or rectal area. When these veins become swollen or irritated, pain results. The treatment by cream or suppository tends to lubricate the anal region reducing irritation and helping make bowel movements less painful. Creams and suppositories may also give comfort for the pain, itching, and discomfort of external and internal hemorrhoids, proctitis, papillitis, cryptitis, anal fissures, incomplete fistulas, pruritus ani and the relief of local pain and discomfort following anorectal surgery. One of the problems in dealing with creams or suppositories is that to place this medication into the anal cavity causes a pain associated with friction. This friction can be between the anal cavity walls and the internal or external hemorrhoids. To solve this problem, lubrication of the suppository or cream insertion device is required. This lubrication can be a messy, sloppy process. Insertion of suppositories in the anal or vaginal region has required use of the lubricated fingers of the patient or nurse to place the suppository in the appropriate position. The present invention provides a device and method for enabling a suppository to be placed into the appropriate body cavity without the patient or nurse touching the suppository. The present invention also provides a device and method for automatically lubricating a suppository applicator.

An object of the present invention is to provide a device which can place a suppository into a cavity in the body without the user or nurse touching the suppository.

Another object of the present invention is to provide a device which can lubricate a cavity in the body in which a suppository is being placed at the time the suppository is being placed therein, without the user or nurse touching the body or the lubricating substance.

A further object of the present invention is to provide a device with a void area or compartment from which a lubricating substance can be propelled at a desired time.

Still another object of the present invention is to provide a plunger with a shaped suppository seat on the end in order to hold and project a suppository completely through the body of a suppository applicator.

Another object of the present invention is to provide a suppository shaft, within a suppository applicator, which extends from one end of the applicator body to the other end, within which the suppository can be placed without touching the suppository and through which the suppository can be propelled to be placed at a desired location.

A further object of the present invention is to provide a lubricating suppository applicator comprised of a body through which a lubricating plunger can force a lubricating substance out from the body prior to a suppository plunger propelling a suppository through the same body.

Still another object of the present invention is to provide a method and means for a void area within the body of a suppository applicator to be filled with a lubricating substance.

Another object of the present invention is to provide a device which can place any desired object into a body cavity; the device comprising an applicator body, a lubricating plunger securable within the applicator body, and an object plunger operative to move the object through the applicator body into the body cavity.

Another object of the present invention is to provide a method and means to retain the lubricating substance within the void area or compartment at the time the lubricating substance is placed into the void area of the body of an applicator and prior to utilizing the lubricating substance.

Still another object of the present invention is to provide lubricating means to lubricate external and internal hemorrhoids and the anal cavity wall when placing a suppository into the anal cavity without touching the suppository or the lubricating substance.

A further object of the present invention is to provide a lubricating suppository applicator which is re-usable and comes apart for cleaning and placing new lubricating substance within the device.

Another object of the present invention is to provide a device and method for keeping the lubricating plunger shaft in a lubricating suppository applicator secured within the body of the lubricating suppository applicator when desired.

Still another object of the present invention is to provide a lubricating suppository applicator with a tapered end portion for easier access into a body cavity.

A further object of the present invention is to provide a tapered end portion on a lubricating plunger in order to fit within the tapered end portion of the body of a lubricating suppository applicator in order to be able to force a lubricating substance out from openings in the tapered portion of the lubricating suppository applicator.

These and other objects and features of the invention will be apparent from the following description and appended claims.

Briefly, the invention is a method and device for placing a suppository into a body cavity. The device comprises an applicator body with a shaft extending from a first open end to a second open end, and a void area surrounding the shaft. The void area may be considered a chamber or a compartment within which the lubricating cream or cream packet may be stored. A lubricating plunger is securable to the applicator body. The lubricating plunger is sized and shaped to fit within the void area. A suppository plunger is sized and shaped to fit within the shaft. The suppository plunger may push the suppository from the first open end, to and out of the second open end, when the device is utilized. When the device is placed within the body cavity, the suppository may be pushed through the second open end and into the body cavity.

The applicator body comprises an elongated body with a plurality of first openings which are open to the void area and to the exterior of the elongated body. A lubricating substance is stored in the void area. The lubricating substance is operative to flow from the void area, through the plurality of first openings, and to the exterior of the elongated body, when the lubricating plunger is placed within the void area. The lubricating substance may be stored within a packet.

The applicator body may further comprise a tapered end portion connected to the elongated body which contains a second open end. A plurality of second openings is located in the tapered end portion.

A lubricating substance may be stored in the void area. The lubricating substance may flow through the plurality of first openings to the exterior of the elongated body, and through the plurality of second openings to the exterior of the tapered end portion, when the lubricating plunger is placed within the void area.

The device may place any object into the body cavity. The device may comprise an applicator body, a lubricating plunger securable within the applicator body, and an object plunger operative to move the object through the applicator body into the body cavity.

The lubricating plunger comprises a lubrication plunger shaft controlled by a lubrication plunger control means. A tapered lubrication end portion is connected to the lubrication plunger shaft. When the lubricating plunger is placed within the void area, the tapered lubrication end portion is placed within the tapered end portion of the applicator body.

The applicator body may further comprise an open retainer cap portion which is securable to the elongated body. The lubricating plunger and the suppository plunger may pass through the open retainer cap portion. The open retainer cap portion may comprise a stop surface. The lubricating plunger may comprise a stop. The lubricating plunger and the open retainer cap portion are loosely connected. When the open retainer cap portion is secured to the applicator body, the lubricating plunger is loosely connected to the applicator body.

The suppository plunger comprises a suppository plunger shaft, a suppository seat shaped to effectively push the suppository, and a suppository plunger control means. The suppository seat, which is shaped to effectively push the suppository, is located on one end of the suppository shaft. The suppository plunger control means is secured to the other end of the suppository plunger shaft.

A sheath is sized and shaped to fit over the applicator body. The sheath covers the plurality of first openings in the elongated body and is securable to the applicator body. The sheath also covers the plurality of second openings in the tapered end portion.

The applicator body further comprises a gripping area which is secured to the end of the elongated body. The gripping area aids in holding and utilizing the device. The open retainer cap portion may be secured to the gripping area.

The lubricating substance may be a medicinal lubricant for treating health problems within the body cavity. A retaining cap may be secured to the bottom of the applicator body to retain the lubricating substance within the void area, when the void area is being filled with lubricating substance. When the void area is being filled with lubricating substance, the sheath may be located over the applicator body to prevent the lubricating substance from passing through the plurality of first openings and second openings.

The method for placing a suppository into a body cavity comprises placing the suppository into the previously described device. The device is then placed into the body cavity. The lubricating plunger is pressed as the device enters the body cavity. The suppository plunger is pushed, thereby pushing the suppository through the device, out of the second open end, and into the body cavity.

The invention will be more fully understood from the following detailed description and appended claims when taken with the drawings in which:

FIG. 1 is an isometric elevational view of suppository applicator 1.

FIG. 2 is a sectional view of the body 2 of suppository applicator 1 showing the insertion of suppository 10.

FIG. 3 is an exploded sectional view showing the alignment of plunger 4, suppository 10, and body 2.

FIG. 4 is a sectional view showing suppository 10 within body 2, with plunger 4 in position within body 2 to eject suppository 10 from body 2.

FIG. 5 is a partial sectional view of suppository applicator 1 inserted between the buttocks 15 into the anal cavity 39.

FIG. 6 is a partial sectional view of suppository applicator 1 showing the suppository 10 injected into the anal cavity 39 prior to the removal of the suppository applicator 1.

FIG. 7 is an isometric elevational view of lubricating suppository applicator 16.

FIG. 8 is an exploded elevational view of lubricating suppository applicator 16 showing sheath 38 below body 17.

FIG. 9 is an elevational view of cream packet 29.

FIG. 10 is a partial sectional view of the lubricating suppository applicator 16 with lubricating cream 37 in cream packet 29 in place, and suppository 10 within body 17 ready for insertion.

FIG. 11 is a partial sectional view of lubricating suppository applicator 16 showing the cream packet 29 ruptured and the lubricating cream 37, within the anal cavity 39, lubricating suppository applicator 16, while the suppository 10 is inserted.

FIG. 13 is a top sectional view of body 17 at section 13-13 of FIG. 8.

FIG. 14 is a top view of lubricating plunger 23.

FIG. 15 is a top view of suppository plunger 26.

Figure 11:
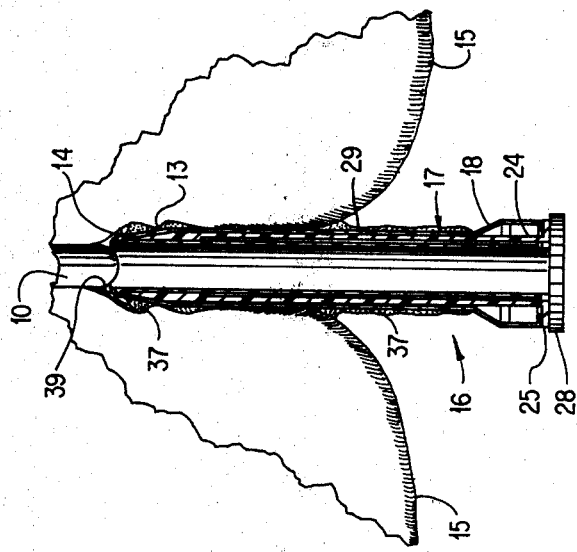

FIG. 16 is an isometric view of void area 41 of body 17 being filled with lubricating cream 37 by an external cream dispenser 43 from an external cream source 42.

FIG. 17 is an isometric view of retaining cap 44 secured onto the gripping area 18 of body 17.

Referring now to the drawings, FIG. 1 is an isometric elevational view of suppository applicator 1. Suppository applicator 1 has a body 2 with a gripping area 3. Plunger 4 fits within body 2. Plunger 4 has a shaft 6 and a control knob 7. Body 2 has an elongated portion 5 and a tapered end 9.

FIG. 2 is a sectional view of the body 2 of suppository applicator 1 showing the insertion of suppository 10. Suppositories today may come packaged in many ways. The suppository 10, therefore, may have some type of suppository cover or wrapper 11. Wrapper 11 may be partially unfolded from suppository 10 without actually touching suppository 10. The suppository 10 may then be placed within the suppository shaft 8 within the body 2 of suppository applicator 1. The suppository 10 may be placed into the suppository shaft 8 with the fingers of the user touching only the wrapper 11. When the suppository 10 is placed fully within the suppository shaft 8, the wrapper 11 can be pulled away.

FIG. 3 is an exploded sectional view showing the alignment of plunger 4, suppository 10, and body 2. Suppository wrapper 11 has been removed and the plunger 4 has been aligned with body 2. Plunger 4 has a shaft 6, a control knob 7, and a shaped suppository seat 12. The shaped suppository seat 12 may be shaped in a manner to properly cup the end of suppository 10 in order to push the suppository 10 through suppository shaft 8 and out of the opening in the end of suppository shaft 8.

FIG. 4 is a sectional view showing suppository 10 within body 2, with plunger 4 in position within body 2 to eject suppository 10 from body 2. The suppository 10 and the plunger 4 are within the suppository shaft 8 within body 2.

FIG. 5 is a partial sectional view of suppository applicator 1 inserted between the buttocks 15 into the anal cavity 39. Within anal cavity wall 14 are shown hemorrhoids 13. The suppository 10 is inserted through the suppository applicator 1 into the anal cavity 39.

FIG. 6 is a partial sectional view of suppository applicator 1 showing the suppository 10 injected in the anal cavity 39 prior to the removal of the suppository applicator 1. The suppository 10 is now in the anal cavity 39 after having been injected through the body 2 of suppository applicator 1. The suppository 10 has been placed into the appropriate position into the anal cavity 39 without the user having ever touched the suppository 10. In utilizing suppository applicator 1, it would be appropriate to lubricate the exterior of body 2. Lubrication can be accomplished by any desired means.

FIG. 7 is an isometric elevational view of lubricating suppository applicator 16. In lubricating suppository applicator 1, no matter how neat the user tries to be, the risk is still prevalent that the user will have to touch the lubricant. Another messy alternative is that the user utilize hands or fingers coated with lubricant and placed into the anal area to lubricate the anal area prior to insertion of the suppository applicator 1. A cleaner and neater alternative is lubricating suppository applicator 16 shown in FIG. 7.

Lubricating suppository applicator 16 has a body 17 and a gripping area 18. Body 17 has an elongated body 19 with a tapered end 22. Body 17 has a suppository shaft 20 and lubricating openings 21 located in the elongated body 19 and in the tapered end 22. The lubricating suppository applicator 16 has a lubricating plunger 23 with a lubrication plunger shaft 24 and lubrication plunger control knob 25. Lubricating suppository applicator 16 has a suppository plunger 26 with a suppository plunger shaft 27 and a suppository plunger control knob 28.

FIG. 8 is an exploded elevational view of lubricating suppository applicator 16 showing sheath 38 below body 17. Lubricating suppository applicator 16 comprises body 17, lubricating plunger 23, and suppository plunger 26. Sheath 38 may be utilized to cover the lubricating openings 21 in body 17 prior to the utilization of the lubricating suppository applicator 16. Sheath 38 may be secured in any manner. A simple friction fit, with the end 40 of sheath 38 fitting closely over gripping area 18 of body 17, would be sufficient. Any other desired means to keep the lubricating openings 21 in body 17 covered may be utilized.

Lubricating plunger 23 has a lubrication plunger shaft 24 with a tapered portion 32. Suppository plunger 26 fits through lubricating plunger 23 and can push a suppository 10 through the suppository shaft 20 in body 17. Suppository shaft 26 has a suppository seat 33 on the end of suppository plunger shaft 27 which can cup and grip a suppository 10 for pushing the suppository 10 through the suppository shaft 20 in body 17.

FIG. 9 is an elevational view of cream packet 29. A cream packet 29, which may be any type of packaging for a lubricating cream, liquid, or ointment, may be utilized within the lubricating suppository applicator 16. If packaging, such as cream packet 29, is utilized, it is placed appropriately within the body 17 and, at the proper time, the cream packet 29 is ruptured by the movement of lubricating plunger 23. A packaging for a cream, liquid, or ointment, such as cream packet 29, may be utilized and all the cream, liquid, or ointment may be placed in the appropriate cavity within body 17.

Figure 10:
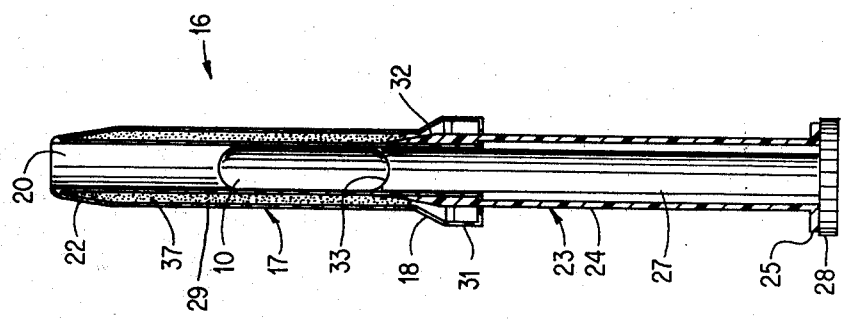

FIG. 10 is a partial sectional view of the lubricating suppository applicator 16 with lubricating cream 37 in cream packet 29 in place, and suppository 10 within body 17 ready for insertion. A suppository 10 is within suppository shaft 20 of body 17. Cream packet 29 is filled with lubricating cream 37. Lubricating plunger 23 is placed within the body 17, through the open retainer cap 31. Open retainer cap 31 is secured onto gripping area 18. Open retainer cap 31 may be secured in any manner to gripping area 18. In FIG. 8, the gripping area 18 is shown having a threaded portion 30 to which the open retainer cap 31 is secured.

The lubricating plunger 23 has a lubrication plunger shaft 24 with a tapered end portion 32. The tapered end portion 32, as the lubricating plunger 23 presses into the body 17, ruptures the cream packet 29, which will cause the lubricating cream 37 to flow through the lubricating openings 21 in body 17.

FIG. 11 is a partial sectional view of lubricating suppository applicator 16 showing the cream packet 29 ruptured and the lubricating cream 37, within the anal cavity 39, lubricating suppository applicator 16, while the suppository 10 is inserted. The lubricating cream 37, within cream packet 29, has coated the exterior of body 17 and is lubricating the anal cavity 39. The lubricating cream 37 is coating the area between the buttocks 15, including the anal cavity wall 14 where hemorrhoids 13 may be present. The lubricating cream 37, having been pressed by the lubricating plunger 23 from the or compartment 41 within body 17, coats around the entire outside surface of body 17. Should there be external or internal hemorrhoids, the lubricating cream 37 would supply a soothing, lubricating action to enable the lubricating suppository applicator 16 to be placed into position for the suppository 10 to be appropriately placed into the anal cavity 39. The design of the lubricating plunger 23 enables the maximum amount of lubricating cream 37, within the void area 41, to be forced through the lubricating openings 21 to the exterior of body 17.

The suppository plunger 26 can push the suppository 10 within the suppository plunger shaft 27 through body 17 and into the anal cavity 39. The suppository shaft 20 within body 17 may be completely free from contact with the void area 41 and the rupturing action caused by the lubricating plunger 23 in void area 41. The lubricating plunger 23 can force the lubricating cream 37 from the void area 41 whether the lubricating cream 37 is in a packet, such as packet 29, or is simply stored within the void area 41.

Figure 12:
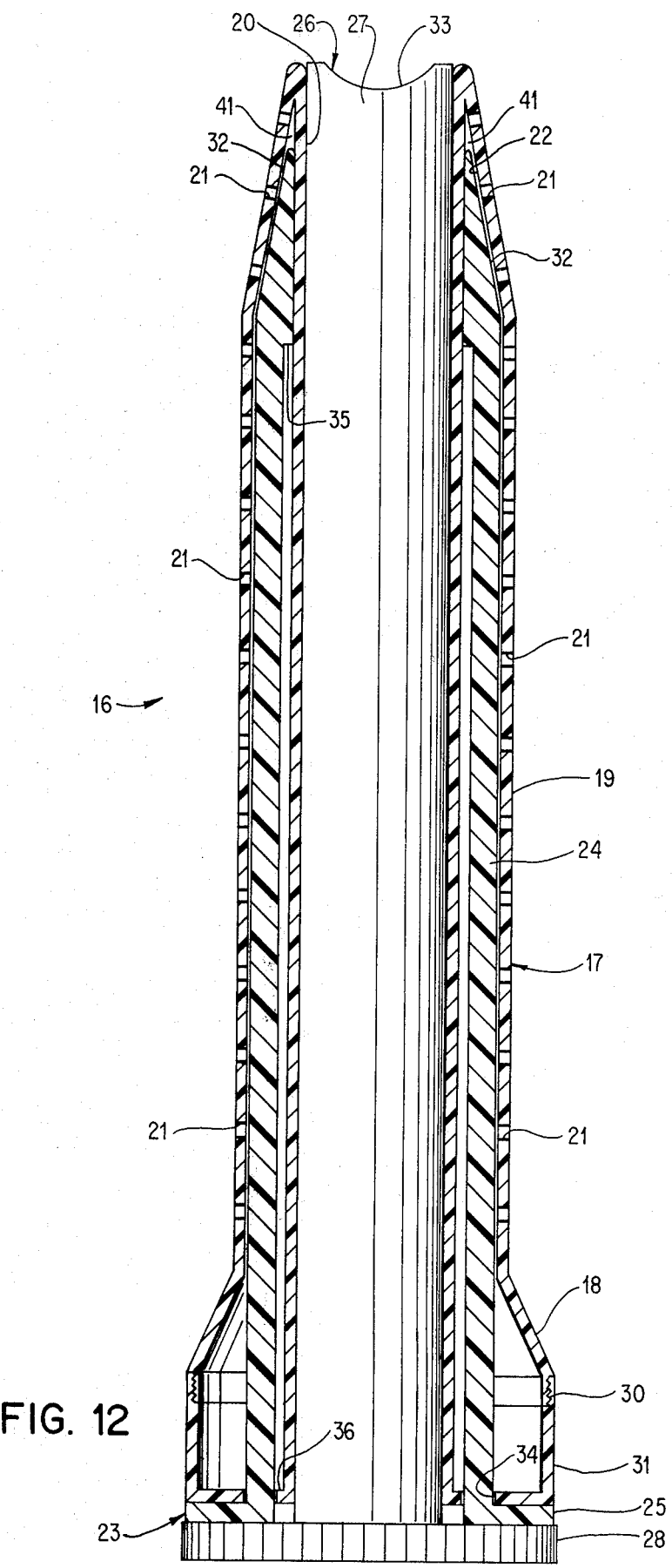
FIG. 12 is an enlarged sectional view of the lubricating suppository applicator 16 in a closed position.

FIG. 12 is an enlarged sectional view of the lubricating suppository applicator 16 in a closed position. The lubrication plunger shaft 24 may be designed to completely fill or almost fill the entire void area 41, thereby utilizing the maximum amount of lubricating cream 37, which is stored within void area 41. The tapered end 22 of body 17, with lubricating openings 21, helps prepare the anal cavity 39 for the entrance of the complete body 17 of lubricating suppository applicator 16. The tapered end portion 32 of lubricating plunger 23 acts, not only as a rupturer of a cream packet 29 or a mover of the lubricating cream 37, but is designed to fit within the tapered end 22 of body 17. The tapered end portion 32 of lubricating plunger 23 will, therefore, press the lubricating cream 37 through the lubricating openings 21 in the tapered end portion 22 of body 17, as well as the lubricating openings 21 in the elongated body 19 of body 17.

The lubricating suppository applicator 16 may be designed to be opened in many different ways. FIG. 12 shows a threaded portion 30 on gripping area 18 to which an open retainer cap 31 is attached. Open retainer cap 31 has a opening 34 extending around the body 17 allowing for the passage of the lubrication plunger shaft 24 of lubricating plunger 23.

The tapered end portion 32 of lubricating plunger 23 has a stop 35, which will press on stop surface 36 within open retainer cap 31, in order to keep the lubricating plunger 23 from coming out of the body 17 of the lubricating suppository applicator 16. When the lubricating suppository applicator 16 is being used, the lubricating plunger 23 presses the lubricating cream 37 onto the anal cavity wall 14 allowing the entrance of the body 17 of the lubricating suppository applicator 16 into the anal cavity 39. The suppository plunger 26 is then moved by suppository plunger control knob 28 to cause the suppository plunger shaft 27 to force the suppository 10 out from the lubricating suppository applicator and into the anal cavity 39.

FIG. 13 is a top sectional view of body 17 at section 13-13 of FIG. 8. In FIG. 13, there is no lubricating cream 37 or cream packet 29 shown in the void area 41. The relationship between the suppository shaft 20 and the void area 41 is shown as the void area 41 completely surrounds the suppository shaft 20. Lubricating openings 21 emanate from the void area 41.

FIG. 14 is a top view of lubricating plunger 23 showing the ideal shape of the lubricating plunger 23.

FIG. 15 is a top view of the suppository plunger 26 showing the ideal shape of the suppository plunger 26.

FIG. 16 is an isometric view of void area 41 of body 17 being filled with lubricating cream 37 by an external cream dispenser 43 from an external cream source 42. The void area 41 in body 17 may be filled with a packet, such as lubricating cream packet 29, or the void area may be filled by cream, liquid, or ointment from an external source, such as external cream source 42. Any type of external cream source 42 or external cream dispenser 43 may be utilized to place the lubricating substance 37 into the void area 41. When placing the lubricating substance 37 into the void area 41, the sheath 38, shown in FIG. 8, may be utilized to cover the lubricating openings 21 in body 17. Open retainer cap 31 may be removed or left in place. To seal the bottom openings in the body 17 of lubricating suppository applicator 16, a retaining cap 44 may be utilized.

FIG. 17 is an isometric view of retaining cap 44 secured onto the gripping area 18 of body 17. Retaining cap 44 may be secured onto the threaded portion 30 of gripping area 18 or may be secured to the gripping area 18 by friction, or other means. The retaining cap 44 may also be secured, if desired, to the open retaining cap 31. The lubricating suppository applicator 16 may, therefore, be re-usable. Lubricating suppository applicator 16 may be taken apart, as shown in FIG. 8, to be cleaned or stored and may be re-supplied with lubricating substance 37 as indicated herein.

The lubricating suppository applicator 16 of this invention may be utilized to place suppositories both anally or vaginally into the orifice of the body. The entrance to the orifice may be lubricated at the time the lubricating suppository applicator 16 is utilized without the user touching either the lubricating substance 37 or the suppository 10.

The present invention provides a device which can place a suppository and a lubricating substance into a body cavity without the user ever having touched the suppository or lubricant. The device provides a method and device for a void area within the device to be filled with a lubricating substance and for that substance to be propelled from the device at a desired time by a lubricating plunger. The device also provides for the lubricating substance to be retained within the void area at the time the lubricating substance is placed into the void area and prior to utilizing the lubricating substance. The device will provide lubricating means to lubricate external and internal hemorrhoids and the anal cavity wall when placing a suppository into the anal cavity. A lubricating suppository applicator is provided which is re-usable and comes apart for cleaning and placing new lubricating substance within the device. The lubricating suppository applicator comprises a body through which a lubricating plunger can force a lubricating substance out from the body prior to a suppository plunger propelling a suppository through the same body.

A suppository shaft is provided, within a suppository applicator, which extends from one end of the applicator body to the other end, within which a suppository can be placed and through which a suppository can be propelled to be placed at a desired location. A suppository seat is provided on the end of a suppository plunger to hold and project a suppository completely through the body of a suppository applicator.

The invention provides a device and method for keeping the lubricating plunger shaft in a lubricating suppository applicator secured within the body of the lubricating suppository applicator, when desired. A taper end portion on a lubricating plunger is also provided in order to fit within the tapered end portion of the body of a lubricating suppository applicator in order to be able to force a lubricating substance out from the openings in the tapered end portion of the lubricating suppository applicator. The lubricating suppository applicator also can be provided with a tapered end portion for easier access into a body cavity.

The present invention enables a suppository to be placed into a body cavity without touching the suppository. The applicator in the present invention can utilize present-day packaging of suppositories to pull apart the outside packaging and push the suppository into the suppository shaft within the body of the present applicator. The plunger of the present applicator can then push the suppository to a position within the shaft of the applicator prior to being pushed out of the other end of the applicator at the desired time.

The applicator may be externally lubricated or the applicator may have an internal lubrication system in which a lubricating substance is stored within the applicator. The lubricating substance will be pressed out of the body of the applicator at a desired time when the applicator is placed in a desired location. The applicator discussed herein can aid in having those persons, who do not wish to manually place a suppository in position or to manually handle a suppository or lubricating substance, to avoid that task.

Many methods will be utilized to place the lubricating substance within the applicator. Various shapes and sizes of applicators will be utilized using the principles of the method and device discussed herein. The method of storing a lubricating substance within an applicator and applying the lubricating substance at a desired time is encompassed by the present invention.

The applicator is shown in the specification to be re-usable. It can, however, be manufactured as a disposable unit, if desired.

The lubricating substance may be any lubricating substance desired, such as K-Y Jelly, or other sterile lubricant. The lubricating substance may also be a cream, liquid, or ointment medicinal lubricant, which would have the additional feature of medically treating the interior anal cavity walls through which the applicator would pass, in order to place the suppository within the anal cavity of the body. External hemorrhoids, which might not receive the desired benefit from a suppository, could be treated by a flowable medicinal substance which could flow through the openings of the body of the applicator. This additional medicinal feature would enable the hemorrhoidal problem to be attacked by a variety of medications. When using the applicator vaginally, a sterile lubricant would probably be most desirable for use in the lubricating suppository applicator. However, other medicines could be utilized if medically advisable.

The applicator discussed herein could be utilized, not only by humans, but for the treatment of animals in veterinary medicine.

The suppository, contemplated for use with the device and defined in the specification and appended claims, could be a suppository utilized for any purpose in any orifice of a body and would include any type of object with mass which might be inserted or injected into an orifice of a body. Suppositories for anal use for hemorrhoids or other problems are within the scope of this invention. Any object, such as a tampon or a birth control means, injected or placed into the vaginal area could be utilized in the manner as illustrated herein.

The applicator body may be any type of body in which a lubricating plunger may be placed and through which an object plunger may pass. The applicator body, discussed in detail herein, has a shaft extending from a first open end to a second open end. A void area surrounds the shaft. The lubricating plunger is securable to the applicator body and is sized and shaped to fit within the void area. The object plunger is sized and shaped to fit within the shaft. Other configurations of an applicator body might be utilized and be within the scope of the present invention and the appended claims.

While the invention has been described with reference to specific embodiments, the description is illustrative and is not to be construed as limiting the scope of the invention. Various modifications and changes may occur to those skilled in the art without departing from the spirit and scope of the invention as defined by the appended claims. The void area may be considered a chamber or a compartment within which the lubricating cream or cream packet may be stored.

I claim:

1. A device for placing a suppository into a body cavity comprising:
   a. an applicator body with a shaft extending from a first open end to a second open end;
   b. a compartment surrounding said shaft;
   c. a lubricating plunger moveably secured to said applicator body, sized and shaped to fit within said compartment; and
   d. a suppository plunger, sized and shaped to fit within said shaft, wherein said suppository plunger may push said suppository from said first open end to and out of said second open end when said device is utilized, whereby when said device is placed within said body cavity, said suppository may be pushed through said second open end into said body cavity.

2. A device according to claim 1 wherein said applicator body comprises an elongated body with a plurality of first openings in said elongated body which are open to said compartment and to the exterior of said elongated body.

3. A device according to claim 2 further comprising a lubricating substance stored in said compartment operative to flow from said compartment, through said plurality of first openings, to said exterior of said elongated body when said lubricating plunger is placed within said compartment.

4. A device according to claim 3 wherein said lubricating substance is stored within a packet.

5. A device according to claim 2 wherein said applicator body further comprises a tapered end portion connected to said elongated body containing said second open end.

6. A device according to claim 5 further comprising a plurality of second openings in said tapered end portion of said applicator body which are open to said compartment and to the exterior of said tapered end portion of said applicator body.

7. A device according to claim 6 wherein said lubricating substance stored in said void area is operative to flow from compartment area through said plurality of first openings to said exterior of said elongated body and through said plurality of second openings to said exterior of said tapered end portion, when said lubricating plunger is placed within said compartment.

8. A device according to claim 6 wherein said lubricating plunger comprises a lubrication plunger shaft controlled by a lubrication plunger control means and a tapered lubrication end portion connected to said lubrication plunger shaft, whereby when said lubrication plunger is placed within said compartment said tapered lubrication end portion is placed within said tapered end portion of said applicator body.

9. A device according to claim 2 wherein said applicator body further comprises an open retainer cap portion securable to said elongated body through which said lubricating plunger and said suppository plunger may pass.

10. A device according to claim 9 wherein said open retainer cap portion comprises a stop surface and said lubricating plunger further comprises a stop secured onto said tapered lubrication end portion, whereby said open retainer cap portion is held loosely with said lubricating plunger, whereby when said open retainer cap portion is secured to said applicator body, said lubricating plunger is loosely connected to said elongated body.

11. A device according to claim 1 wherein said suppository plunger comprises a suppository plunger shaft, a suppository seat shaped to effectively push said suppository on one end of said suppository shaft, and said suppository plunger control means secured to the other end of said suppository plunger shaft.

12. A device according to claim 2 further comprising a sheath, sized and shaped to fit over said applicator body, covering said plurality of first openings in said elongated body and securable to said applicator body.

13. A device according to claim 6 further comprising a sheath, sized and shaped to fit over said applicator body, covering said plurality of first openings in said elongated body and said plurality of second openings in said tapered end portion and securable to said applicator body.

14. A device according to claim 2 wherein said applicator body further comprises a gripping area secured to the end of said elongated body containing said first open end and operative to aid in holding and utilizing said device.

15. A device according to claim 14 further comprising an open retainer cap portion securable to said gripping area through which said lubricating plunger and said suppository plunger may pass.

16. A device according to claim 3 wherein said lubricating substance is a medicinal lubricant for treating health problems within said body cavity.

17. A device according to claim 2 further comprising a retaining cap securable to the bottom of said applicator body to retain said lubricating substance within said compartment, when said compartment has been filled with said lubricating substance.

18. A device according to claim 17 further comprising a sheath, sized and shaped to fit over said applicator body, covering said plurality of first openings in said elongated body and securable to said applicator body, whereby when said compartment is filled with said lubricating substance, said sheath will prevent said lubricating substance from passing through said plurality of first openings and said retaining cap will prevent said lubricating substance from escaping through said bottom of said applicator body.

19. A device according to claim 6 further comprising a retaining cap securable to the bottom of said applicator body to retain said lubricating substance within said compartment, when said compartment has been filled with said lubricating substance.

20. A device according to claim 19 further comprising a sheath, sized and shaped to fit over said applicator body, covering said plurality of first openings in said elongated body and said plurality of second openings in said tapered end portion and securable to said applicator body, whereby when said compartment is filled with said lubricating substance, said sheath will prevent said lubricating substance from passing through said plurality of first and second openings and said retaining cap will prevent said lubricating substance from escaping through said bottom of said applicator body.

21. A method for placing a suppository into a body cavity comprising:
  a. placing said suppository into a device comprising:
    (1) an applicator body with a shaft extending from a first open end to a second open end;
    (2) a compartment surrounding said shaft;
    (3) a lubricating plunger moveably secured to said applicator body, sized and shaped to fit within said compartment; and
    (4) a suppository plunger, sized and shaped to fit within said shaft, wherein said suppository plunger may push said suppository from said first open end to and out of said second open end when said device is utilized;
  b. placing said device into said body cavity;
  c. pressing said lubricating plunger as said device enters said body cavity; and
  d. pushing said suppository plunger, thereby pushing said suppository through said device, out of said second open end, and into said body cavity.

22. A method according to claim 21 wherein said applicator body comprises an elongated body with a plurality of first openings in said elongated body which are open to said compartment and to the exterior of said elongated body.

23. A method according to claim 22 wherein said device further comprises a lubricating substance stored in said void area operative to flow from said compartment, through said plurality of first openings, to said exterior of said elognated body when said lubricating plunger is placed within said compartment.

24. A method according to claim 23 wherein said lubricating substance is stored within a packet.

25. A method according to claim 22 wherein said applicator body further comprises a tapered end portion connected to said elongated body containing said second open end.

26. A method according to claim 25 wherein said device further comprises a plurality of second openings in said tapered end portion of said applicator body which are open to said compartment and to the exterior of said tapered end portion of said applicator body.

27. A method according to claim 26 wherein said lubricating substance stored in said compartment is operative to flow from said compartment through said plurality of first openings to said exterior of said elongated body and through said plurality of second openings to said exterior of said tapered end portion, when said lubricating plunger is placed within said compartment.

28. A method according to claim 26 wherein said lubricating plunger comprises a lubricating plunger shaft controlled by a lubrication plunger control means and a tapered lubrication end portion connected to said lubrication plunger shaft, whereby when said lubrication plunger is placed within said compartment, said tapered lubrication end portion is placed with said tapered end portion of said applicator body.

29. A method according to claim 22 wherein said applicator body further comprises an open retainer cap portion securable to said elongated body through which said lubricating plunger and said suppository plunger may pass.

30. A method according to claim 29 wherein said open retainer cap portion comprises a stop surface and said lubricating plunger further comprises a stop secured onto said tapered lubrication end portion, whereby said open retainer cap portion is held loosely with said lubricating plunger, whereby when said open retainer cap portion is secured to said applicator body, said lubricating plunger is loosely connected to said elongated body.

31. A method according to claim 21 wherein said suppository plunger comprises a suppository plunger shaft, a suppository seat shaped to effectively push said suppository on one end of said suppository shaft, and said suppository plunger control means secured to the other end of said suppository plunger shaft.

32. A method according to claim 22 wherein said device further comprises a sheath, sized and shaped to fit over said applicator body, covering said plurality of first openings in said elongated body and securable to said applicator body.

33. A method according to claim 26 wherein said device further comprises a sheath, sized and shaped to fit over said applicator body, covering said plurality of first openings in said elongated body and said plurality of second openings in said tapered end portion and securable to said applicator body.

34. A method according to claim 22 wherein said applicator body further comprises a gripping area secured to the end of said elongated body containing said first open end and operative to aid in holding and utilizing said device.

35. A method according to claim 24 wherein said device further comprises an open retainer cap portion securable to said gripping area through which said lubricating plunger and said suppository plunger may pass.

36. A method according to claim 23 wherein said lubricating substance is a medicinal lubricant for treating health problems within said body cavity.

37. A method according to claim 22 wherein said device further comprises a retaining cap securable to the bottom of said applicator body to retain said lubricating substance within said compartment, when said compartment has been filled with said lubricating substance.

38. A method according to claim 37 wherein said device further comprises a sheath, sized and shaped to fit over said applicator body, covering said plurality of first openings in said elongated body and securable to said applicator body, whereby when said compartment is filled with said lubricating substance, said sheath will prevent said lubricating substance from passing through said plurality of first openings and said retaining cap will prevent said lubricating substance from escaping through said bottom of said applicator body.

39. A method according to claim 26 wherein said device further comprises a retaining cap securable to the bottom of said applicator body to retain said lubricating substance within said compartment, when said compartment has been filled with said lubricating substance.

40. A method according to claim 39 wherein said device further comprises a sheath, sized and shaped to fit over said applicator body, covering said plurality of first openings in said elongated body and said plurality of second openings in said tapered end portion and securable to said applicator body, whereby when said compartment is filled with said lubricating substance, said sheath will prevent said lubricating substance from passing through said plurality of first and second openings and said retaining cap will prevent said lubricating substance from escaping through said bottom of said applicator body.

41. A device for placing an object into a body cavity comprising:
 a. an applicator body;
 b. a lubricating plunger moveably secured within said applicator body; and
 c. an object plunger, moveably secured within said applicator body, sized and shaped to fit within said applicator body, wherein said object plunger may move said object out of said applicator body when said device is utilized, whereby when said device is placed within said body cavity, said object may be moved into said body cavity.

42. A device according to claim 41 wherein said applicator body comprises an elongated body with a plurality of first openings in said elongated body which are open to said applicator body and to the exterior of said elongated body.

43. A device according to claim 42 further comprising a lubricating substance stored in said applicator body operative to flow from said applicator body, through said plurality of first openings, to said exterior of said elongated body, when said lubricating plunger is placed within said applicator body.

44. A device according to claim 43 wherein said lubricating substance is stored within a packet.

45. A device according to claim 42 wherein said applicator body further comprises a tapered end portion connected to said elongated body.

46. A device according to claim 45 further comprising a plurality of second openings in said tapered end portion of said applicator body which are open to the exterior of said tapered end portion of said applicator body.

47. A device according to claim 46 wherein said lubricating substance stored in said applicator body is operative to flow from said applicator body, through said plurality of first openings to said exterior of said elongated body, and through said plurality of second openings to said exterior of said tapered end portion, when said lubricating plunger is placed within said applicator body.

48. A device according to claim 46 wherein said lubricating plunger comprises a lubrication plunger shaft controlled by a lubrication plunger control means and a tapered lubrication end portion connected to said lubrication plunger shaft, whereby when said lubrication plunger is placed within said applicator body, said tapered lubrication end portion is placed within said tapered end portion of said applicator body.

49. A device according to claim 42 wherein said applicator body further comprises an open retainer cap portion securable to said elongated body through which said lubricating plunger and said object plunger may pass.

50. A device according to claim 49 wherein said open retainer cap portion comprises a stop surface and said lubricating plunger further comprises a stop secured onto said tapered lubrication end portion, whereby said open retainer cap portion is held loosely with said lubricating plunger, whereby when said open retainer cap portion is secured to said applicator body, said lubricating plunger is loosely connected to said elongated body.

51. A device according to claim 41 wherein said object plunger comprises an object plunger shaft, an object seat shaped to effectively move said object on one end of said object shaft, and said object plunger control means secured to the other end of said object plunger shaft.

52. A device according to claim 42 further comprising a sheath, sized and shaped to fit over said applicator body, covering said plurality of first openings in said elongated body and securable to said applicator body.

53. A device according to claim 46 further comprising a sheath, sized and shaped to fit over said applicator body, covering said plurality of first openings in said elongated body and said plurality of second openings in said tapered end portion and securable to said applicator body.

54. A device according to claim 42 wherein said applicator body further comprises a gripping area secured to the end of said elongated body operative to aid in holding and utilizing said device.

55. A device according to claim 54 further comprising an open retainer cap portion securable to said gripping area through which said lubricating plunger and said object plunger may pass.

56. A device according to claim 43 wherein said lubricating substance is a medicinal lubricant for treating health problems within said body cavity.

57. A device according to claim 42 further comprising a retaining cap securable to the bottom of said applicator body to retain said lubricating substance within said applicator body, when said applicator body contains said lubricating substance.

58. A device according to claim 57 further comprising a sheath, sized and shaped to fit over said applicator body, covering said plurality of first openings in said elongated body and securable to said applicator body, whereby when said applicator body contains said lubricating substance, said sheath will prevent said lubricating substance from passing through said plurality of first openings and said retaining cap will prevent said lubricating substance from escaping through said bottom of said applicator body.

59. A device according to claim 46 further comprising a retaining cap securable to the bottom of said applicator body to retain said lubricating substance within said applicator body, when said applicator body contains said lubricating substance.

60. A device according to claim 59 further comprising a sheath, sized and shaped to fit over said applicator body, covering said plurality of first openings in said elongated body and said plurality of second openings in said tapered end portion and securable to said applicator body, whereby when said applicator body contains said lubricating substance, said sheath will prevent said lubricating substance from passing through said plurality of first and second openings and said retaining cap will prevent said lubricating substance from escaping through said bottom of said applicator body.

* * * * *